United States Patent
Ito et al.

(10) Patent No.: US 7,008,225 B2
(45) Date of Patent: Mar. 7, 2006

(54) TOOTH BRUSHER

(75) Inventors: Kazumasa Ito, Aichi (JP); Nobuhiro Takeda, Aichi (JP)

(73) Assignee: Ricoh Elemex Corporation, Aichi (JP)

( * ) Notice: Subject to any disclaimer, the term of this patent is extended or adjusted under 35 U.S.C. 154(b) by 366 days.

(21) Appl. No.: 10/433,979

(22) PCT Filed: Dec. 19, 2001

(86) PCT No.: PCT/JP01/11136

§ 371 (c)(1),
(2), (4) Date: Jun. 10, 2003

(87) PCT Pub. No.: WO02/056727

PCT Pub. Date: Jul. 25, 2002

(65) Prior Publication Data

US 2004/0067466 A1    Apr. 8, 2004

(30) Foreign Application Priority Data

Jan. 22, 2001    (JP)    ................................ 2001-012866

(51) Int. Cl.
*A61C 17/02*    (2006.01)
*A61C 3/03*    (2006.01)
(52) U.S. Cl. .................. 433/120; 433/80; 601/160
(58) Field of Classification Search ................ 433/120, 433/118, 124, 80; 601/162–163, 165
See application file for complete search history.

(56) References Cited

U.S. PATENT DOCUMENTS

| 1,005,024 A | * | 10/1911 | Griner | 601/88 |
| 3,178,754 A | * | 4/1965 | Cleverdon | 15/344 |
| 3,214,775 A | * | 11/1965 | Murov et al. | 15/22.1 |
| 4,179,765 A | * | 12/1979 | Teague et al. | 15/22.1 |
| 4,630,326 A | * | 12/1986 | Stevens | 15/22.1 |

FOREIGN PATENT DOCUMENTS

| JP | 9-322823 | 12/1997 |
| JP | 2000-139966 | 5/2000 |
| JP | 2000-352370 | 12/2000 |

* cited by examiner

*Primary Examiner*—John J Wilson
(74) *Attorney, Agent, or Firm*—Smith, Gambrell & Russell, LLP

(57) ABSTRACT

A safe brushing is realized without sticking the gum if the bristle tips are once inserted in a pocket of a tooth by using a system having a brush of which the bristle tips automatically vibrate in a direction at right angles with the direction of length of the bristles. A brush lever 5 having a brush 4 is swingingly supported in the nozzle 1, a flow passage 3 leading to a blow-out port 1a at an end of a nozzle 1 is partly bent, and a resilient member 7 is provided at the bent portion to urge the brush lever 5 in a direction opposite to the direction of flow of water, so that the brush lever 5 oscillates reciprocally due to the resilient force produced by the resilient member 7 and the pressure of water flow, causing the bristle tips of the brush 4 to oscillate in a direction at right angles with the direction of length of the bristles outside the nozzle 1.

2 Claims, 6 Drawing Sheets

TOOTH BRUSHER

TECHNICAL FIELD

The present invention relates to a tooth-brushing device suited for the prevention and therapy of pyorrhea alveolaris and decayed teeth by conducting the brushing using a brush protruded beyond a nozzle while blowing out water from a blow-out port of the nozzle.

BACKGROUND ART

It has been widely known that sordes on teeth are difficultly removed from such portions as gum grooves among the teeth and pockets deep in the gum grooves. In order to remove sordes on teeth, in general, attempts have been made to conduct the brushing by so contriving the shape of bristle tips of a tooth brush that the bristles can be easily inserted in the gum grooves. With this method, however, a persevering manual work must be conducted for every portion requiring a brushing time of not less than one hour, and a person finds himself tired on his arm consuming too much time and finds it not easy to continue the work any longer.

To solve this problem, Japanese Patent No. 2663213 teaches a tooth-brushing device in which a cylindrical portion of a large diameter is formed in a water passage near the end of a water-injection nozzle, means is provided for reciprocally driving a piston body held in the cylindrical portion, whereby the end of a bundle of stiff bristles held on the front surface of the piston body is caused to reciprocally move in the direction of length of the bristles to go in and out of the blow-out port at the end of the nozzle.

With the system in which the end of the bundle of stiff bristles goes in and out of the blow-out port at the end of the nozzle in the direction of length of the bundle of stiff bristles, however, the moving distance of the bristle tips varies in the direction of length of the bristles. Therefore, it becomes highly probable that the bristle tips are stuck to the inflamed gum causing a severe pain not only when the patient brushes his teeth by himself but also when the patient has his teeth brushed by an expert such as a dentist.

It is therefore a first object of the present invention to realize a safe brushing without sticking the gum if the bristle tips are once inserted in a pocket of a tooth by using a system having a brush of which the bristle tips automatically vibrate in a direction at right angles with the direction of length of the bristles due to the flow of water.

A second object is to efficiently wash, out of the pocket, the sordes and foul matter peeled off the tooth surfaces due to the brushing by concentrating the water flow blown out from the nozzle onto the bristle tips of the brush.

A third object is to realize a safe brushing without sticking the gum if the bristle tips are once inserted in a pocket of a tooth by using a system having a brush that automatically revolves due to the flow of water.

A fourth object is to realize a safe brushing without sticking the gum if the bristle tips are once inserted in a pocket of a tooth by using a system having a brush of which the bristle tips automatically vibrate in a direction at right angles with the direction of length of the bristles due to the flow of water, the system having a simplified internal structure.

DISCLOSURE OF THE INVENTION

The invention described in claim 1 is to accomplish the above first object, and is concerned with a tooth-brushing device for conducting the brushing with a brush protruded beyond a nozzle while blowing out water from a blow-out port of the nozzle, wherein a brush lever having the brush is swingingly supported in the nozzle, a flow passage leading to the blow-out port is partly bent, a resilient member is provided at the bent portion to urge the brush lever in a direction opposite to the direction of flow of water, so that the brush lever oscillates reciprocally due to the resilient force produced by the resilient member and the pressure of water flow. Thus, the bristle tips of the brush automatically oscillate in a direction at right angles with the direction of length of the bristles due to the flow of water. Therefore, if the bristle tips are once inserted in the pocket of the tooth, then, the brushing is safely conducted without sticking the gum.

In the invention described in claim 2, water blown out from the blow-out port is directed to the end of the brush in addition to the constitution of the invention of claim 1. Thus, water blown out from the blow-out port is directed to the end of the brush making it possible to concentrate the water flow blown out from the nozzle onto the bristle tips of the brush and, hence, to efficiently wash, out of the pocket, the sordes and foul matter peeled off the tooth surface by brushing.

The invention described in claim 3 is to accomplish the third object, and is concerned with a tooth-brushing device for conducting the brushing with a brush protruded beyond a nozzle while blowing out wat r from a blow-out port of the nozzle, wherein a brush rotary shaft having the brush is rotatably supported by bearings being deviated from a center axis of the nozzle, and a water-wheel is secured to the brush rotary shaftso as to be rotated by the pressure of water flow. Therefore, if the bristle tips are once inserted in the pocket of the tooth, then, the brushing is safely conducted without sticking the gum. The invention described in claim 4 is to accomplish the fourth object, and is concerned with a tooth-brushing device for conducting the brushing with a brush protruded beyond a nozzle while blowing out water from a blow-out port of the nozzle, wherein a flow passage leading to the blow-out port is bent, a brush lever provided with the brush at an end thereof is bent along the flow passage and is arranged in the flow passage so as to oscillate in a direction at right angles with the direction of length of bristles of the brush, a piston is provided at the other end of the brush lever, and a resilient member is provided to urge the piston in a direction opposite to the direction of water flow, so that the brush lever oscillates reciprocally due to the resilient force produced by the resilient member and the pressure of water flow. Thus, the bristle tips of the brush automatically oscillate in a direction at right angles with the direction of length of the bristles due to the flow of water. Therefore, if the bristle tips are once inserted in the pocket of the tooth, then, the brushing is safely conducted without sticking the gum. Further, the internal structure is simplified since there is no need of holding the brush lever using bearings.

BEST MODE FOR CARRYING OUT THE INVENTION

Embodiments of the invention will now be described in detail with reference to the drawings.

Figure 1:
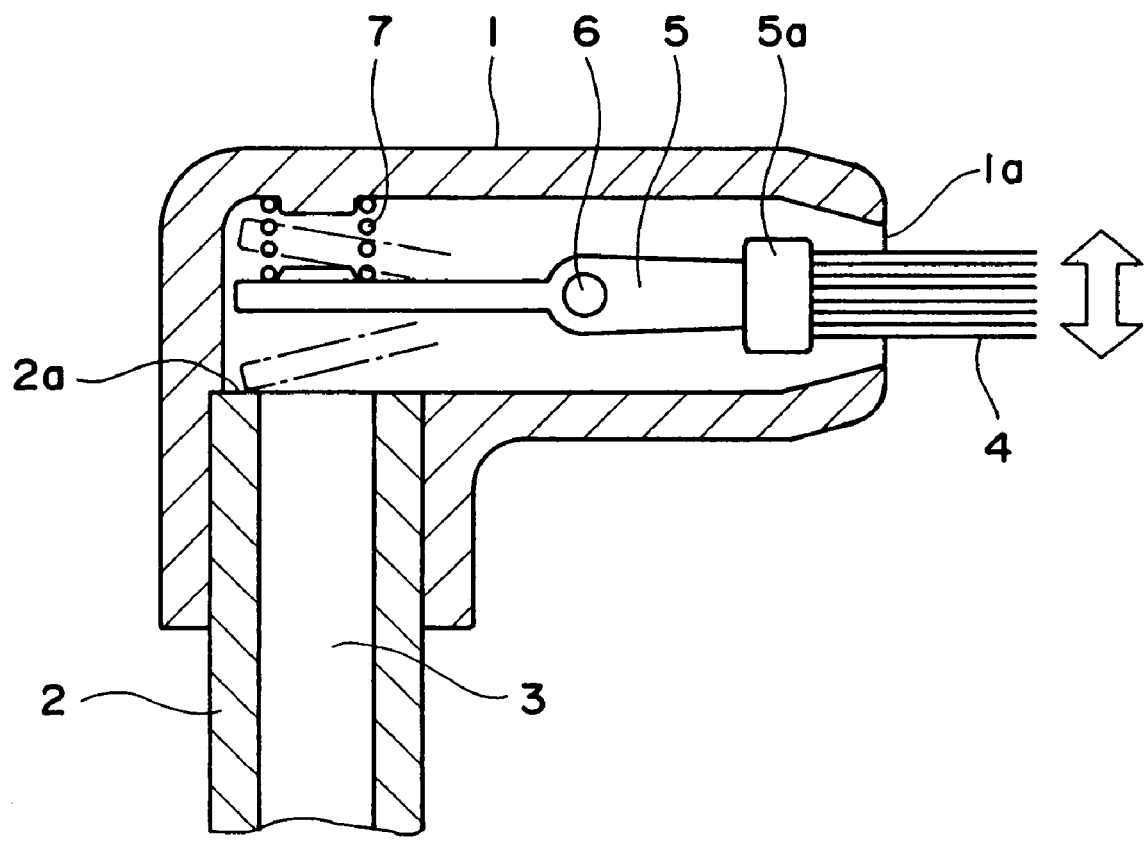
FIG. 1 is a sectional view illustrating a first embodiment of the invention.

FIG. 1 illustrates a first embodiment of the invention, i.e., an embodiment of the invention of claim 1. A nozzle 1 is secured to an end of a main body 2 nearly at right angles therewith, and a flow passage 3 leads to a blow-out port 1a open at an end of the nozzle 1 while being bent nearly at right angles as it goes to the blow-out port 1a from the main body 2.

Inside the nozzle 1, a brush lever 5 holding a brush 4 at an end core 5a is rotatably supported at its middle portion by a pin 6. The brush 4 is partly protruding maintaining a sufficiently large gap relative to the blow-out port 1a. On the side opposite to the brush 4, a compression coil spring 7 is acting on the rear potion of the brush lever 5, the compression coil spring 7 being a resilient member with its one end being secured to the inner wall surface of the nozzle 1. The rear portion of the brush lever 5 is urged in a direction against the flow of water from the main body 2 due to the compression coil spring 7.

According to the structure of FIG. 1, the brush lever 5 is usually pushed by the compression coil spring 7 onto the end 2a of the main body 2. Upon receiving the pressure of water flowing from the side of the main body 2, however, the brush lever 5 turns with the pin 6 as a fulcrum up to a point where a balance is maintained between the pressure of water and the resilient pressure by the compression coil spring 7. Then, due to a change in the pressure of water flow, the brush lever 5 is pushed back again by the compression coil spring 7. As this operation is repeated, the brush lever 5 reciprocally turns repetitively, and the bristle tips of the brush 4 oscillate in a direction at right angles with the direction of length of bristles outside the nozzle 1 while water is blown out from the blow-out port 1a.

Figure 2:
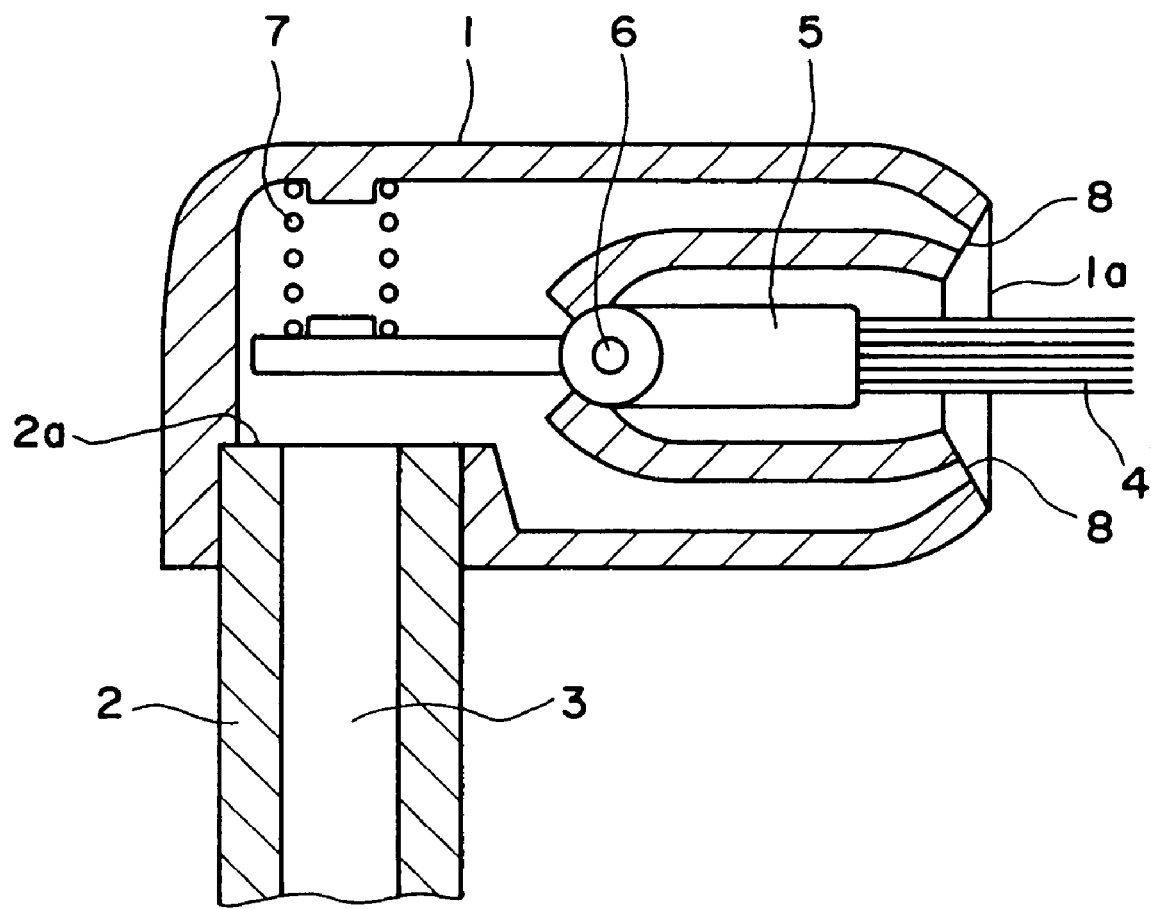
FIG. 2 is a sectional view illustrating a second embodiment of the invention.
Figure 3:
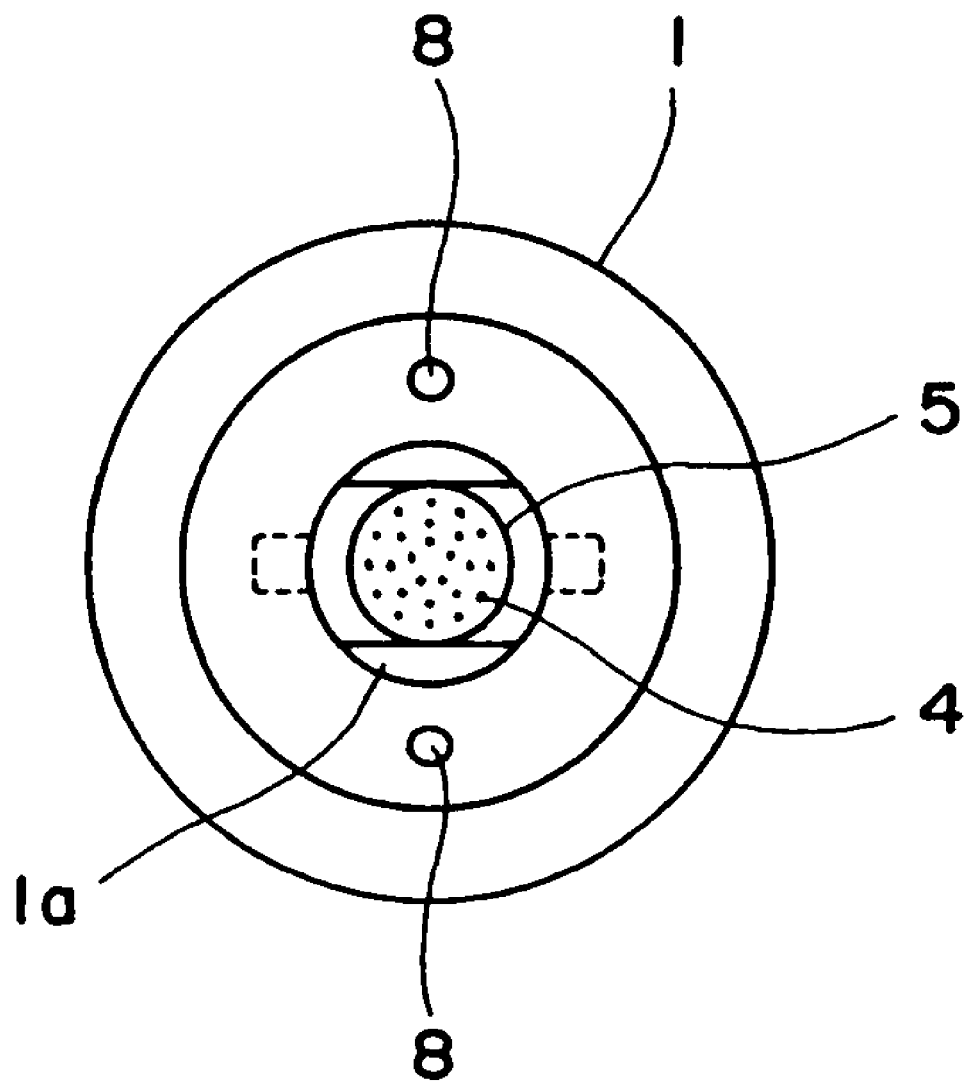
FIG. 3 is a front view of a nozzle.

FIGS. 2 and 3 illustrate a second embodiment of the invention, i.e., an embodiment of the invention of claim 2. In this embodiment, the opening 1a at the end of the nozzle 1 is not for blowing out the water but is simply for permitting the brush 4 to protrude in contrast with the structure of FIG. 1. Instead, a plurality of blow-out ports 8 are formed to surround the opening 1a. Water from the flow passage 3 flows being branched into these blow-out ports 8 and is blown out simultaneously being directed to the end of the brush 4.

Figure 4:
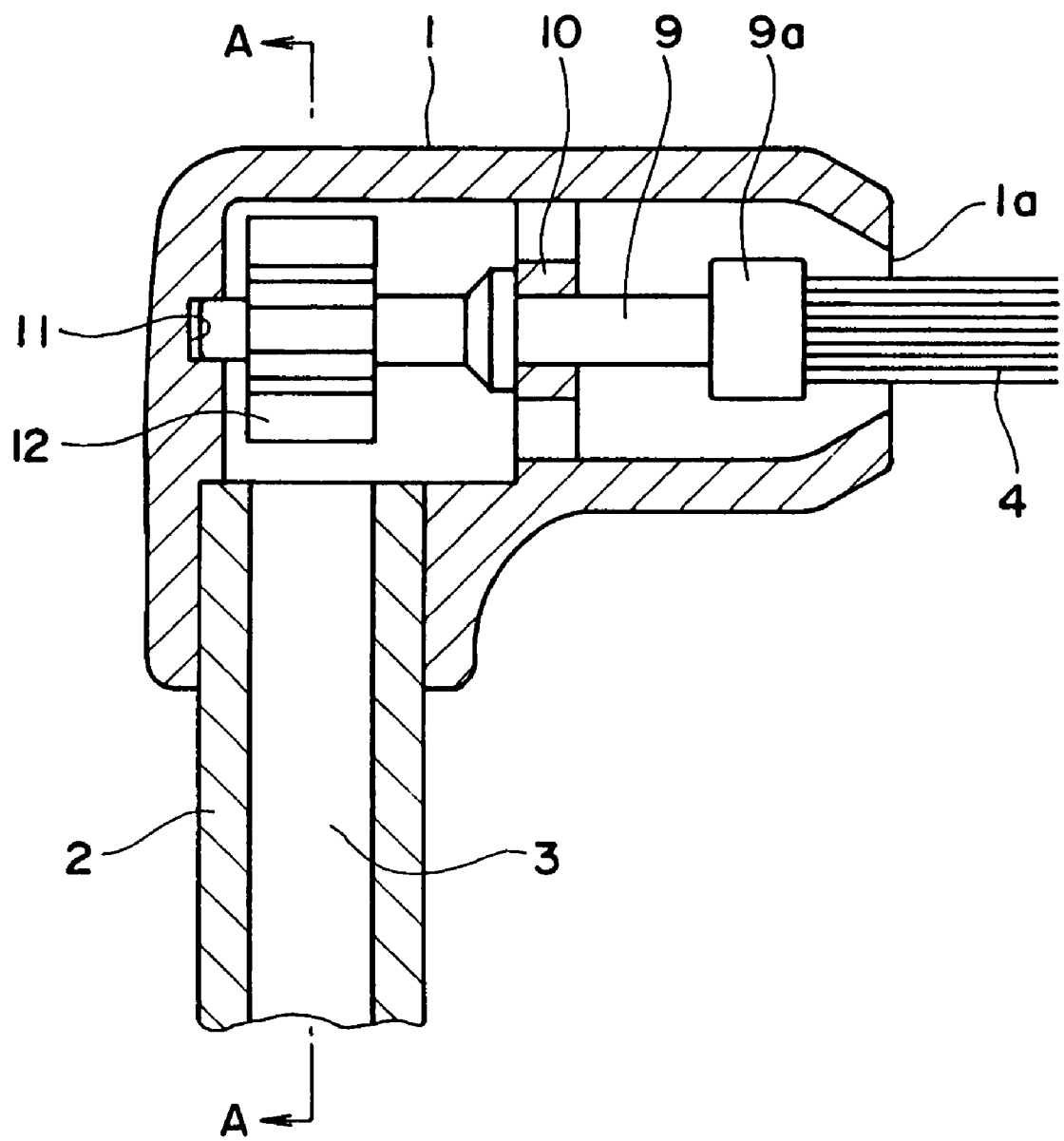
FIG. 4 is a sectional view illustrating a third embodiment of the invention.
Figure 5:
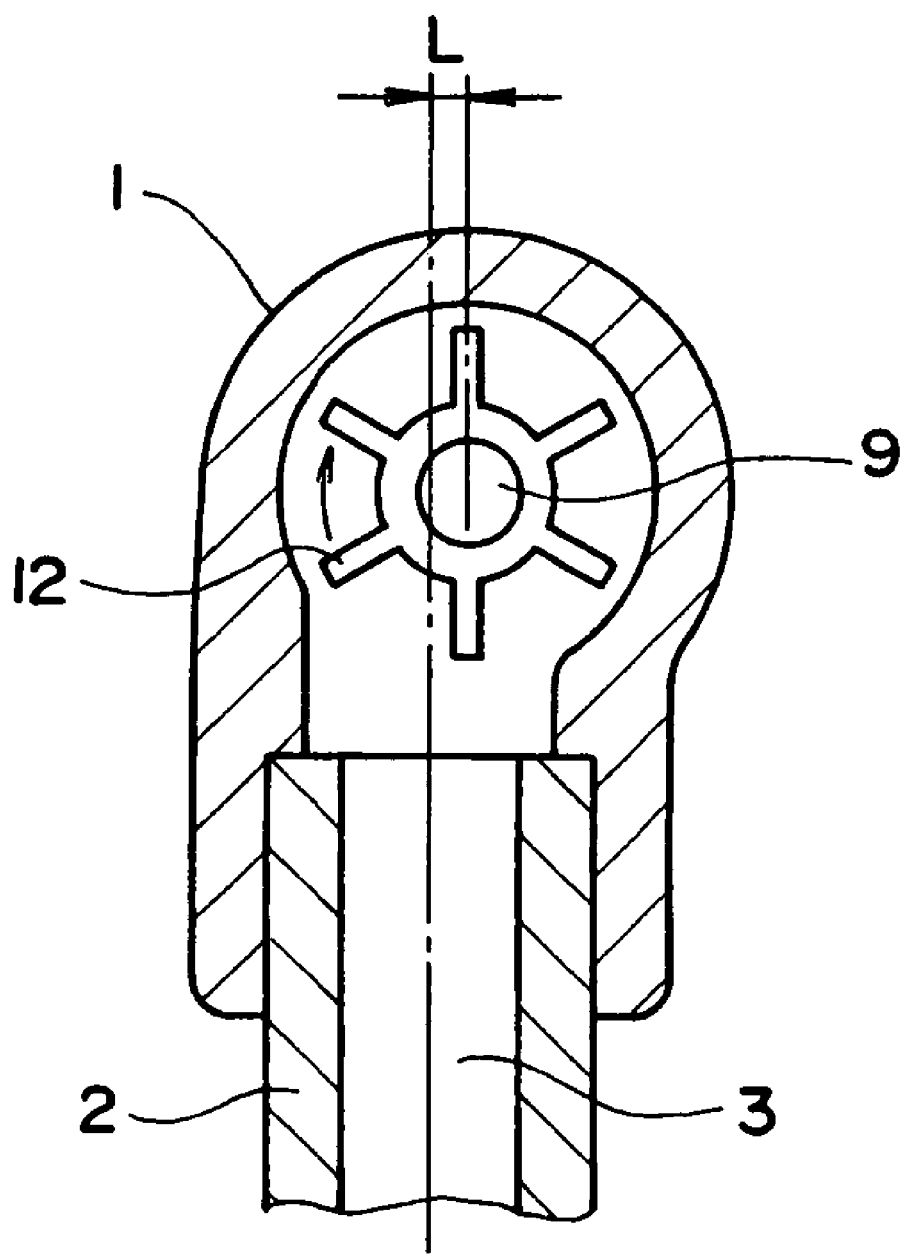
FIG. 5 is a sectional view along the line A—A.

FIGS. 4 and 5 illustrate a third embodiment of the invention, i.e., an embodiment of the invention of claim 3. This embodiment uses a brush rotary shaft 9 holding the brush 4 at an end core 9a instead of the brush lever 5. A middle portion of the brush rotary shaft 9 is supported by a bearing 10 in the nozzle 1, and a rear end thereof is supported by a bearing in a recessed portion 11 in the wall in the nozzle, so that the brush rotary shaft 9 rotates being deviated by a distance L from the center axis of the flow passage 3 in the main body 2. A water-wheel 12 is secured to the brush rotary shaft 9 so as to receive the pressure of water flowing from the main body 2.

According to the structure shown in FIGS. 4 and 5, the water-wheel 12 receives the pressure of water flowing through the flow passage 3 in a deviated state. Therefore, the brush 4 rotates together with the brush rotary shaft 9 while water is blown out from the blow-out port 1a. In this case, the rotary motion can be converted into vibration of the bristle tips of the brush 4 in a direction at right angles with the direction of length of the bristles accompanying the rotation by using a motion converter mechanism that converts the rotary motion into a reciprocal motion by using a link mechanism and an eccentric cam.

Figure 6:
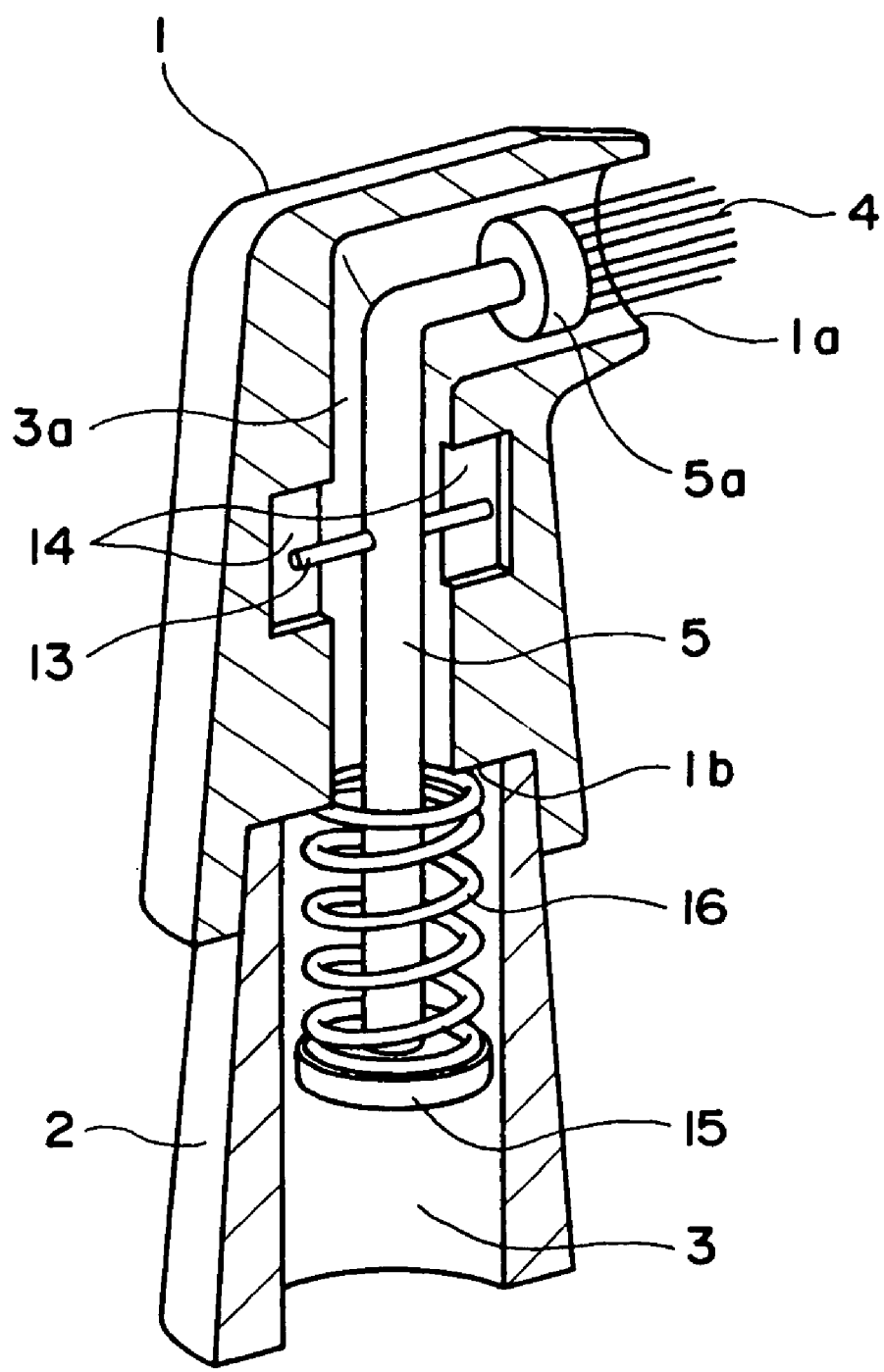
FIG. 6 is a sectional view illustrating a fourth embodiment of the invention.

FIG. 6 illustrates a fourth embodiment of the invention, i.e., an embodiment of the invention of claim 4. In this embodiment, the nozzle 1 itself is formed in an inverse L-shape to bend the flow passage 3a in the nozzle 1, and the brush lever 5 is bent along the flow passage 3a. A pin 13 penetrates through a middle portion of the brush lever 5 at right angles, and guide grooves 14 are formed in the middle portion of the flow passage 3a to guide the pin 13, so that the brush lever 5 is allowed to reciprocally oscillate in a direction at right angles with the direction of length of bristles of the brush lever 5. Further, a piston 15 is provided at the rear end of the brush lever 5, and a compression coil spring 16 which is a resilient member is provided between the piston 15 and the base end 1b of the nozzle 1.

According to the structure of FIG. 6, the brush lever 5 is usually pushed down by the compression coil spring 16. Upon receiving the pressure of water flowing from the side of the main body 2, however, the piston 15 is pushed up to a point where a balance is maintained between the pressure of water and the elastic pressure by the compression coil spring 16. Then, when the pressure of water flow changes, the piston 15 is pushed back again by the compression coil spring 16. As this operation is repeated, the brush lever 5 reciprocally oscillates repetitively, and the bristle tips of the brush 4 oscillate in a direction at right angles with the direction of length of bristles outside the nozzle 1 while water is blown out from the blow-out port 1a.

INDUSTRIAL APPLICABILITY

The invention is concerned with a tooth-brushing device such as an electric tooth brush for household and dental uses, for brushing the teeth while blowing out water.

What is claimed is:

1. A tooth-brushing device for conducting the brushing with a brush protruded beyond a nozzle while blowing out water from a blow-out port of the nozzle, wherein a brush lever having the brush is swingingly supported in the nozzle, a flow passage leading to the blow-out port is partly bent, a resilient member is provided at the bent portion to urge the brush lever in a direction opposite to the direction of flow of water, so that the brush lever oscillates reciprocally due to the resilient force produced by the resilient member and the pressure of water flow.

2. A tooth-brushing device according to claim 1, wherein water blown out from the blow-out port is directed to the end of the brush.

* * * * *